United States Patent [19]

Merger et al.

[11] Patent Number: 5,399,705
[45] Date of Patent: Mar. 21, 1995

[54] 1,1'-BIS(3-AMINOPROPYL)-2,2'-DIIMIDAZOLE

[75] Inventors: Franz Merger, Frankenthal; Klaus Ebel, Mutterstadt; Martin Brudermueller, Mannheim, all of Germany

[73] Assignee: BASF Aktiengesellschaft, Ludwigshafen, Germany

[21] Appl. No.: 122,806

[22] Filed: Sep. 16, 1993

Related U.S. Application Data

[63] Continuation of Ser. No. 960,775, Oct. 14, 1992, abandoned.

[30] Foreign Application Priority Data

Oct. 22, 1991 [DE] Germany ............... 41 34 808.7

[51] Int. Cl.⁶ ......................................... C07D 403/04
[52] U.S. Cl. .............................................. 548/313.4
[58] Field of Search ................................... 548/313.4

[56] References Cited

U.S. PATENT DOCUMENTS 4,576,957  3/1986  Marsico, Jr. et al. ............ 548/262.8

FOREIGN PATENT DOCUMENTS 239246  9/1987  European Pat. Off. .
2149825  4/1972  Germany .

OTHER PUBLICATIONS

H. F. Mark, et al., Encyclopedia of Polymer Science and Engineering, vol. 6 (1986) pp. 348–353.
Chemical Abstracts, vol. 89 (1978) Abstract No. 139603e.
Yamauchi et al I, "Synthesis of 6,7,8,9-tetrahydro, etc" CA 84:121785c (1976).
Yamauchi et al. II, "Reactivity of 2,4(5)-dialkylimidazoles, etc" CA 85:177382g (1976).
Sawa et al, "Synthesis of imidazole compounds, etc" CA 71:101773a (1969).
Houben–Weyl, vol. 11/1, pp. 545–569 (1955).
Organic Syntheses 27 (1947) pp. 18–20.
Organic Reactions 5 (1942) pp. 79–135.
Melloni et al. Arzneim. Forschung 25 (1975) pp. 9–14.

*Primary Examiner*—Patricia L. Morris
*Attorney, Agent, or Firm*—John H. Shurtleff

[57] ABSTRACT

1,1'-bis(3-aminopropyl)-2,2'-diimidazole of the formula I

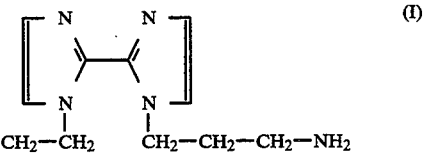

is prepared by a novel process in which 2,2'-diimidazole of the formula II

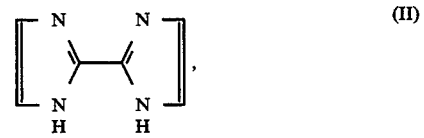

is reacted with acrylonitrile of the formula III

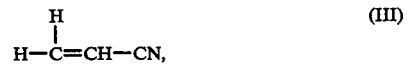

in the presence of basic catalysts at from 80° to 150° C., and hydrogenation is carried out with excess hydrogen in the presence of ammonia on catalysts which contain cobalt, nickel, ruthenium and/or noble metals at from 40° to 200° C. under from 10 to 200 bar.

1 Claim, No Drawings

1,1'-BIS(3-AMINOPROPYL)-2,2'-DIIMIDAZOLE

This application is a continuation of application Ser. No. 07/960,775, filed Oct. 14, 1992, now abandoned.

The present invention relates to novel 1,1'-bis(3-aminopropyl)-2,2'-diimidazole and to a process for preparing it from 2,2'-diimidazole.

Imidazoles which are suitable as epoxy catalysts are disclosed in Handbook of thermoset plastics, Sidney M. Goodman, published by Noyes Publ. Partridge, N.J.

Methods for the aminating hydrogenation of dinitriles are disclosed in Houben-Weyl vol. 11/1, pages 545–569. Alpha,omega-dinitriles such as octamethylene dicyanide can be hydrogenated on catalysts such as Raney nickel at 100° C. in the presence of hydrogen and ammonia (Org. Syntheses 27 (1947) 18).

Org. Reactions 5 (1942) 79–135 discloses the cyanoethylation of nitrogen heterocycles. Furthermore, Arzneim. Forschung 25 (1975) 9–14 and DE-A 21 49 825 disclose the mono- and biscyanoethylation of 2,2'-diimidazole in a 0.1–0.2 molar solution in dimethylformamide in the presence of sodium hydroxide solution as catalyst. The disadvantage of the processes described above is the low concentration, i.e. the large amount of solvent used, and the poor space-time yield associated therewith.

It is an object of the present invention to find novel 2,2'-diimidazoles which have improved properties, and to remedy the abovementioned disadvantages in the process for preparing dinitriles.

We have found that this object is achieved by the novel 1,1'-bis(3-aminopropyl)-2,2'-diimidazole of the formula I

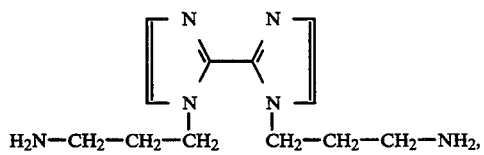

and by a novel process for preparing 1,1'-bis(3-aminopropyl)-2,2'-diimidazole of the formula I, which comprises reacting 2,2'-diimidazole of the formula II

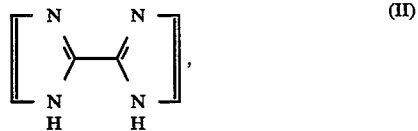

with acrylonitrile of the formula III

in the presence of basic catalysts at from 80° to 150° C., and hydrogenating with excess hydrogen in the presence of ammonia on catalysts which contain cobalt, nickel, ruthenium and/or noble metals at from 40° to 200° C. under from 10 to 200 bar.

The process according to the invention can be carried out as follows:

a) 2,2'-diimidazole II can be reacted in the presence of a basic catalyst and in the presence or absence of an inert solvent at from 80° to 150° C., preferably 80° to 110° C. The pressure during this reaction is not critical and is generally from 0.1 to 50 bar, preferably from 0.5 to 5 bar, particularly preferably atmospheric pressure. The cyanoethylation of 2,2'-diimidazole can be carried out in solution or in suspension, preferably in suspension. Examples of suitable inert solvents are formamides such as dimethylformamide, and aromatic hydrocarbons such as toluene or the xylenes, preferably dimethylformamide. Normally, 0.5–5 l of an inert solvent per mole of 2,2'-diimidazole are employed. Suitable catalysts are basic compounds such as alkali metal or alkaline earth metal hydroxides or substituted and unsubstituted ammonium hydroxides, e.g. quaternary ammonium hydroxides such as tetramethylammonium hydroxide, tetraethylammonium hydroxide, tetrabutylammoniumhydroxide and tetra(2-hydroxyethyl)ammonium hydroxide in amounts of from 0.1 to 20%, preferably 0.5 to 10%, particularly preferably 1 to 5%, of the weight of 2,2'-diimidazole.

b) The hydrogenation can be carried out batchwise or continuously, e.g. in stirred autoclaves at from 40° to 200° C., preferably from 70° to 150° C., under from 10 to 200 bar of hydrogen, preferably 50 to 150 bar, and in the presence of from 20 to 200% by weight of liquid ammonia. Suitable catalysts are those containing cobalt, nickel, for example Raney cobalt or Raney nickel, ruthenium and/or noble metals, for example palladium on carbon. Examples of suitable solvents are aliphatic alcohols, e.g. $C_1$–$C_{20}$-alkanols such as methanol, ethanol, propanol or isopropanol, and ethers such as tetrahydrofuran or dioxane, or mixtures thereof.

2,2'-Diimidazole can be prepared from glyoxal and ammonia or ammonium salts in yields of around 25% (Liebigs Ann. Chem. 605 (1957) 32–35). Preparation from dibromoacetaldehyde and ammonia gives yields of around 30%, and synthesis from hydroxyethylenediamine hydrochloride gives a yield of 60% (Khimiya Geterotsiklicheskikh Soedinenii 8 (1987) 1069–1070). 2,2'-Diimidazole bis(hydrogen sulfate) is obtained in 85% yield from glyoxal sulfate (Khimiya Geterot. Soedinenii 8 (1987) 1069–1070). Yields above 80% are obtained by reacting methyl diiminoglyoxylate with aminoacetaldehyde dimethyl acetal (Synthesis (1986) 336–337).

1,1'-Bis(3-aminopropyl)-2,2'-diimidazole has a wide variety of uses, inter alia as epoxy catalyst, as diamine for novel polyamides with imidazole structural units, and as complexing agent for numerous applications, such as in corrosion prevention.

EXAMPLES

Example 1

A suspension of 500 g of 2,2'-diimidazole (2.2 mol) and 20 g of tetramethylammonium hydroxide in 1000 ml of dimethylformamide in a stirred reactor is heated to 100° C. and 240 g of acrylonitrile are metered in over the course of 10 minutes. The mixture is stirred at 75° C. for 3 hours, and the homogeneous solution is cooled with ice. The precipitated solid, 450 g of 1,1'-bis(2-cyanoethyl)-2,2'-diimidazole, is filtered off with suction and washed with ether (melting point 210°–212° C., yield 84%).

Example 2

A 2.5 l stirred autoclave is charged with 400 g of 1,1'-bis(2-cyanoethyl)-2,2'-diimidazole, 80 g of Raney cobalt, 250 ml of liquid ammonia and 500 ml of tetrahydrofuran. The reaction is complete after 10 hours at 150° C. under 150 bar of hydrogen. Filtration and distillation (boiling point 215° C./1 mbar) result in 330 g of 1,1'-bis(3-aminopropyl)-2,2'-diimidazole as colourless oil (yield 80%).

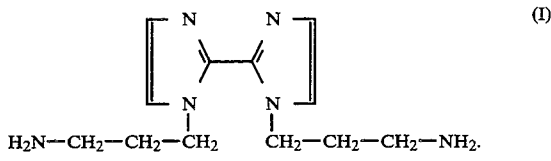

We claim:

1. 1,1'-Bis(3-aminopropyl)-2,2'-diimidazole of the formula I